United States Patent [19]

Campo

[11] Patent Number: 5,100,653
[45] Date of Patent: Mar. 31, 1992

[54] TOPICAL COMPOSITIONS FOR TREATING MOUTH TISSUES

[76] Inventor: Giovanni Campo, Largo Corsia dei Servi, 11, 20122 Milano, Italy

[21] Appl. No.: 652,921

[22] Filed: Feb. 8, 1991

[51] Int. Cl.$^5$ .................. A61K 7/22; A61K 33/04
[52] U.S. Cl. ........................................ 424/54; 424/49
[58] Field of Search ..................... 424/49-58

[56] References Cited

FOREIGN PATENT DOCUMENTS 242553 10/1987 European Pat. Off. .
326884  8/1989 European Pat. Off. .

OTHER PUBLICATIONS

Campo, C.A. 112:124959v (1990) of EP 326,884 8 Aug. 1989.
Campo, et al, C.A. 108:624972 (1988), of EP. 242553 28 Oct. 1987.

*Primary Examiner*—Shep K. Rose
*Attorney, Agent, or Firm*—Robert W. Fiddler

[57] ABSTRACT

A pharmaceutical product for topical treatment of diseases and infections of parodental areas in which trometamol in a concentration of less than 3% is combined with sulfur and allantoin to obtain the desired acid neutralizing effects of trometamol without the undesired side effects.

7 Claims, No Drawings

TOPICAL COMPOSITIONS FOR TREATING MOUTH TISSUES

This invention relates to compositions for the treatment of inflamed and/or infected tissue, and more particularly to a topical pharmaceutical composition to maintain the health of mouth tissues and promote the healing of any damaged tissue.

BACKGROUND OF THE INVENTION

The gums or periodontal tissues of those suffering gum and other diseases of the oral cavity often become inflamed and subject to laceration and bleeding. Under such circumstances, maintenance of desired oral hygiene is difficult, and patients find it painful to maintain desired dental hygiene by brushing and flossing the teeth.

With a view to obviating the above problem, a variety of compositions have in the past been evolved combining a variety of healing and pain relieving agents.

Thus, Gault in U.S. Pat. No. 3,929,555 discloses a speckle particle for addition to a dentrifice in which allantoin, aluminum dihydroxy allantoinate or aluminum chlorhydroxy allantoinate is employed to promote healing and to combat sensitivity of dental tissue.

Lukaschek et al in German published patent application 24 29 035 filed June 18, 1974; and Hofacker in German published patent application 25 29 271 filed July 1, 1975 also disclose the desirability of using allantoin in mouth and dental care compounds.

In Vol. 37, No. 2, p. 129 of Soap, Perfumes and Cosmetics of Feb. 1964, Mecca discloses the desirability of combining sulfur with allantoin to treat acne. Gearheart in U.S. Pat. No. 1,558,160 discloses the use of sulfur in a gum massage preparation, and in Chemical Abstract, Vol. 89, 1978, there is a reference to Nomura's disclosure of combining allantoin and sulfur to treat athlete's foot.

Notwithstanding the above prior art, there has been no successful use of compositions containing sulfur and allantoin to treat oral cavity tissues.

Further, it has been recognized that desired healing is promoted by eliminating acid from the areas to be treated. Though a variety of antacids are available, it has been discovered that trometamol, chemically known as trihydroxymethylaminomethane is more effective than sodium bicarbonate in buffering metabolic acids when used in neonatal asphyxia. (See Martindale, The Extra Pharmacopoeia, 27th Ed., 1977, pp. 570–571.)

It is also known as discussed in the above Martindale reference that with trimetamol solutions of more than 3.6% in water, tissue damage may occur in the event of extravasation at the injection site of an injection of a trimetamol solution.

SUMMARY OF THE INVENTION

According to the invention, it has been discovered that the desired properties of trometamol in buffering metabolic acids such as occur in the mouth may be obtained without facing known undesired side effects previously encountered in the use of trometamol. This is accomplished by employing trometamol in concentrations of less than 3% in preparations containing sulfur and allantoin. This creates a topical product eminently suitable for treatment of gum diseases such as gingivitis, stomatitis, pyorrhea, aphthae and other diseases and/or infections of the parodental areas.

Effective and enduring neutralization of acidity is obtained serving to eliminate tissue irritations which can promote and aggravate ailments characterized by burning sensations, lesions, etc.

Additionally, the addition of trometamol to the trophic preparations containing sulfur and allantoin creates optimal therapeutic conditions for the cicatrization, regeneration and lenitive activities which are the desired effects produced by said preparations.

SPECIFIC PREFERRED EMBODIMENTS

The ratios between the sulfur and allantoin in the preparations are not critical. Sulfur may be used in concentrations varying from 0.1% to 99.0%; and allantoin from 0.1% to 15.0%. However, so as to avoid previously known undesired side effects arising in the use of trometamol, it has been found that desired antacid conditions may be obtained without undesired side effects by employing trometamol in concentrations from 0.1% to 3.0%.

The sulfur is preferably elemental sulfur, and may be in the form of cyclohexasulfur, cycloheptasulfur, alpha, beta or gamma sulfur, cubic cyclooctasulfur, cyclodecasulfur, fibrous sulfur, colloidal sulfur, etc.

The allantoin may be in the form of aluminum dihydroxy allantoinate or aluminum chlor hydroxyallantoinate.

Chemically compatible excipients may be used, such as talcs, lactose, clays, flavorings, dyes, etc. to form powders. Or in forming pastes or gels, liquid suspension, emulsifiers, aggregating agents, and flavorings and coloring agents may be used.

Therapeutically complementary substances such as vitamins, antibiotics, chemotherapeutic, antimycotic, antiviral and antibacterial products in general, analgesic astringents, amino acids and cicatrizants may be added to the topical pharmaceutial preparations for odontostomatological use, which are the subject of this invention.

It is intended that the compositions here disclosed may be incorporated in a toothpaste.

| EXAMPLES OF RATIOS BETWEEN THE ACTIVE INGREDIENTS (SULFUR, ALLANTOIN AND TROMETAMOL) IN THE BASIC PREPARATIONS AND IN COMBINATION WITH OTHER ACTIVE INGREDIENTS AND EXCIPIENTS. | | | | | |
|---|---|---|---|---|---|
| EXAMPLE NO. | SULFUR g | ALLANTOIN g | TROMETAMOL g | OTHER NOTE | EXCIPIENTS NOTE |
| 1 | 99 | 0.5 | 0.5 | | |
| 2 | 40 | 5.0 | 3.0 | | (a) |
| 3 | 45 | 5.0 | 3.0 | (b) | (c) (a) |
| 4 | 40 | 1.0 | 0.5 | (d) | |
| 5 | 40 | 1.0 | 1.0 | (e) | (f) |
| 6 | 20 | 0.5 | 3.0 | | (g) (h) (a) |
| 7 | 45 | 5.0 | 3.0 | (i) | (a) |
| 8 | 30 | 1.58 | 0.1 | (j) | (a) |

-continued

EXAMPLES OF RATIOS BETWEEN THE ACTIVE INGREDIENTS (SULFUR, ALLANTOIN AND TROMETAMOL) IN THE BASIC PREPARATIONS AND IN COMBINATION WITH OTHER ACTIVE INGREDIENTS AND EXCIPIENTS.

| EXAMPLE NO. | SULFUR g | ALLANTOIN g | TROMETAMOL g | OTHER NOTE | EXCIPIENTS NOTE |
|---|---|---|---|---|---|
| 9  | 30 | 1.58 | 0.5 | (k)     | (a) |
| 10 | 3  | 0.5  | 0.5 | (l)     | (a) |
| 11 | 30 | 5.0  | 1.0 | (m) (n) | (a) |
| 12 | 30 | 5.0  | 0.5 | (o)     | (a) |

(a) Rice starch - balance needed to produce 100 g of the preparation
(b) Sodium chloride - 3 g
(c) Kaolin bolus alba - 30 g
(d) Sodium ascorbate - 1.76 g
(e) Calcium pantothenate - 1 g
(f) Lactose - balance needed to produce 100 g of the preparation
(g) Colloidal silicon hydrate - 1.5 g
(h) Mint alcohol - 0.2 g
(i) Lidocaine chloral hydrate - 1 g
(j) Methionine - 1.49 g
(k) Chlorhexidine - 5.05 g
(l) Nystatin - 200,000 units
(m) Idoxuridine - 1.5 g
(n) Neomycin sulfate - 0.6 g
(o) Zinc citrate - 0.1 g Formation of the above compositions are affected employing conventional production techniques utilizing conventional mixing techniques.

The above disclosure has been given by way of illustration, and not by way of limitation, and it is desired to protect all embodiments of the here disclosed invention within the scope of the appended claims.

What is claimed is:

1. A topical composition for the treatment of odontostomatological conditions by application of the composition to teeth, gums and adjacent areas in the oral cavity, said composition comprising as active ingredients allantoin and sulfur, to which has been added trometamol in a concentration of 0.1% to 3%.

2. A composition as in claim 1 in which sulfur is present as alpha, beta or gamma sulfur, fibrous sulfur, insoluble sulfur or colloidal sulfur.

3. A composition as in claim 1 in which allantoin is present in the form of an allantoinate.

4. A composition as in claim 1 in which excipients selected from one or more of: rice starch, kaolin bolus alba, lactose, colloidal silicon hydrate or mint alcohol are selected.

5. A composition as in claim 1 in which additives selected from one or more of: sodium chloride, sodium ascorbate, calcium pantothenate, lidocaine chloral hydrate, methionine, chlorhexidine, nystatin, idoxuridine, neomycin sulfate, or zinc are selected.

6. A toothpaste containing the composition of claim 1.

7. A toothpaste containing the composition of claim 5.

* * * * *